United States Patent [19]

Selva et al.

[11] Patent Number: 5,843,679
[45] Date of Patent: Dec. 1, 1998

[54] METHOD FOR SELECTIVELY ENHANCING THE PRODUCTION OF FACTORS A OR $B_0$ OF ANTIBIOTIC A 40926 COMPLEX

[75] Inventors: Enrico Selva, Via Di Vittorio; Luciano Gastaldo, Via San Martino; Maurizio Denaro, Viale Bligny; Giovanni Cassani, Via Vittadini; Francesco Parenti, Via Benvenuto Cellini, all of Italy

[73] Assignee: Biosearch Italia S.p.A., Varese, Italy

[21] Appl. No.: 460,024

[22] Filed: Jun. 2, 1995

Related U.S. Application Data

[63] Continuation of Ser. No. 258,907, Jun. 10, 1994, abandoned, which is a continuation of Ser. No. 140,363, Oct. 20, 1993, abandoned, which is a continuation of Ser. No. 866,075, Apr. 1, 1992, abandoned, which is a continuation of Ser. No. 519,338, May 2, 1990, abandoned, which is a continuation of Ser. No. 95,371, Sep. 10, 1987, abandoned.

[30] Foreign Application Priority Data

Sep. 11, 1988 [GB] United Kingdom .................... 8621912

[51] Int. Cl.⁶ ...................................... C12P 21/04
[52] U.S. Cl. ............................ 435/71.3; 435/75; 435/76; 435/244; 435/169
[58] Field of Search ............................... 435/71.3, 75, 76, 435/244, 169, 725

[56] References Cited

U.S. PATENT DOCUMENTS

| | | |
|---|---|---|
| 4,698,418 | 10/1987 | Malabarba et al. . |
| 4,782,042 | 11/1988 | Selva ............................................ 514/9 |
| 4,868,171 | 9/1989 | Selva et al. . |
| 4,927,754 | 5/1990 | Assi et al. ............................... 435/71.3 |
| 4,994,555 | 2/1991 | Panzone et al. . |
| 5,194,424 | 3/1993 | Malabarba et al. . |
| 5,486,465 | 1/1996 | Giantonio et al. . |
| 5,567,676 | 10/1996 | Selva et al. . |
| 5,594,102 | 1/1997 | Panzone et al. . |
| 5,606,036 | 2/1997 | Hermann et al. . |

FOREIGN PATENT DOCUMENTS

| | | |
|---|---|---|
| 85112406.5 | 1/1985 | European Pat. Off. . |
| 0177882 | 4/1986 | European Pat. Off. . |

OTHER PUBLICATIONS

Chemical Abstracts, vol. 101, No. 7, Aug. 13, 1984 p. 318, abstract No. 51459t.

The Journal of Antibiotics, 1984, 37 (5), 494–502., Omura et al.

*Primary Examiner*—Irene Marx
*Attorney, Agent, or Firm*—Killworth, Gottman, Hagan & Schaeff, L.L.P.

[57] ABSTRACT

The present invention is directed to a method for selectively enhancing the production of factors A, and/or $B_0$ of antibiotic A 40926 either to isolate these single components in better yields or to enrich the complex in one or both the above components, which comprises adding an appropriate precursor of the desired antibiotic factor to an A 40926 producing culture during fermentation.

9 Claims, No Drawings

5,843,679

METHOD FOR SELECTIVELY ENHANCING THE PRODUCTION OF FACTORS A OR $B_0$ OF ANTIBIOTIC A 40926 COMPLEX

This is a continuation of application Ser. No. 08/258,907, filed Jun. 10, 1994, now abandoned, which is a continuation of application Ser. No. 08/140,363, filed Oct. 20, 1993, now abandoned, which is a continuation of application Ser. No. 07/866,075, filed Apr. 1, 1992, now abandoned, which is a continuation of application Ser. No. 07/519,338, filed May 2, 1990, now abandoned, which is a continuation of application Ser. No. 07/095,371, filed Sep. 10, 1987, now abandoned, which is herein incorporated by reference.

Antibiotic A 40926 is a glycopeptidic antibiotic which has been isolated from a culture of Actinomadura, named Actinomadura sp. ATCC 39727. It is a complex whose factors have been named factor A, factor B, factor $B_0$, factor PA and factor PB. It was described in EP-A-177882 which corresponds to U.S. Pat. No. 4,935,238. The chemical structure of these factors is given in European Patent Application 0 228 015, which was published on Jul. 8, 1987.

This antibiotic complex as well as the single factors thereof bind to D-Alanyl-D-Alanine terminating oligopeptides and are mainly active against gram-positive bacteria and Neisseriae.

The present invention is directed to a method for selectively enhancing the production of factors A, and/or $B_0$ of antibiotic A 40926 either to isolate these single components in better yields or to enrich the complex in one or both the above components, which comprises adding an appropriate precursor of the desired antibiotic factor to an A 40926 producing culture during fermentation.

According to the method of the invention, it is in fact possible, for instance, to modulate the ratio of the single major components of antibiotic A 40926 complex in large scale industrial fermentation. This method therefore represents a useful tool to adjust the composition of the final product to adhere to standard specifications.

Moreover, by following the procedure of the invention it is also possible to obtain, directly from the fermentation mass of the producing strain, a crude product very rich in antibiotic A 40926 factor A or $B_0$ which can then be isolated in a pure form with higher yields and less time consuming steps.

A further object of the present invention is a method for enhancing the production of A 40926 factors PA and/or PB. It is known from EP-A- 177882 that these two factors are natural "precursors" of antibiotic A 40926 factors A and $B_0$, respectively. Therefore, by conducting the recovery of the antibiotic substances with a limited exposition to basic conditions, a complex will be obtained which is enriched in factor PA and/or PB instead of factor A and/or $B_0$. More particularly, the appropriate precursor enhancing the production of antibiotic A 40926 factor PA is the same as that for antibiotic A 40926 factor A and the appropriate precursor for factor PB is the same as that for antibiotic A 40926 factor $B_0$.

The appropriate precursor for increasing the ratio of factor $B_0$ in antibiotic A 40926 complex is selected from valine, its salts with acid and bases which are non-toxic to the producing microorganism, alpha-keto-isovaleric acid, its salts with bases which are non-toxic to the producing microorganism, its esters with mono- and poly-hydroxy lower alkanols, isobutyric acid, its salts with bases which are non-toxic to the producing microorganism, its esters with mono- and poly-hydroxy lower alkanols, isobutanol and its esters with acids which are non-toxic to the producing microorganism.

The appropriate precursor for increasing the ratio of factor A in antibiotic A 40926 complex is selected from n-propanol and its esters which are non-toxic to the producing microorganism, propionic acid, its salts with bases which are non-toxic to the producing microorganism, its esters with mono- or poly-hydroxy lower alkanols, isoleucine, its salts with acids and bases which are non-toxic to the producing microorganism, alpha-keto-beta-methylvaleric acid, its salts with bases which are non-toxic to the producing microorganism, its esters with mono- and poly-hydroxy lower alkanols, 2-methylbutyric acid, its salts with bases which are non-toxic to the producing microorganism, its esters with mono- and poly-hydroxy lower alkanols, 2-methylbutanol and its esters with acids which are non-toxic to the producing microorganism, and any other substance which is capable of being transformed into propionyl-Coenzime A under the fermentation conditions.

Salts with bases which are non-toxic to the microorganism are salts wherein the type and concentration of the given cation is such that it does not impair either the growth of the microorganism culture or the production of the desired antibiotic substance to a considerable extent at the concentration employed in the fermentation mass. Examples of said cations are those from alkali metals and alkaline earth metals such as sodium, potassium, calcium or magnesium, as well as those from amines, such as ammonium, primary, secondary or tertiary $(C_1-C_4)$alkyl ammonium and hydroxy $(C_1-C_4)$alkyl ammonium. Preferred salts are those with sodium, potassium or ammonium ions.

Examples of salts with acids which are non-toxic to the producing microorganism, i.e. salts with acids which do not either impair considerably the growth of the microorganism culture or the production of the desired antibiotic substance, at the concentration at which they are present in the fermentation mass, are preferably mineral acids such as hydrochloric acid, even if also organic acids may, in some instances, be present.

Esters of an appropriate precursor as defined above with mono- and poly-hydroxy lower alkanols are esters with $(C_1-C_6)$alkanols with 1, 2, 3, 4, 5 or 6 hydroxy functions per molecule. When $(C_1-C_4)$alkanols are used, they must be different from those which act as precursors for the other antibiotic factor (i.e. isobutanol or 2-methylbutanol) unless concomitant increase of both factors is desired.

Preferred examples of poly-hydroxy alkanols are glycerol and propylene glycol.

When the lower alkanol may be present in different enantiomeric and epimeric forms, in the present description and claims, each single form separately as well as the mixture of said single form in any proportion is intended.

Esters of an appropriate hydroxy containing precursor as defined above which are non-toxic to the microorganism are $(C_2-C_{22})$alkanoyl esters wherein the type and concentration of the alkanoyl moiety in the fermentation medium is such that it does not impair the growth of the microorganism culture or the production of the desired antibiotic substance to a considerable extent. In general, straight chain $(C_2-C_4)$ alkanols are preferred.

An antibiotic A 40926 producing culture is a culture of a strain like Actinomadura sp. ATCC 39727 or a producing mutant or variant thereof, which is capable, upon cultivation, of producing recoverable amounts of antibiotic A 40926.

The method of the invention includes cultivating an antibiotic A 40926 producing culture in an aqueous nutrient culture medium containing an assimilable source of carbon, an assimilable source of nitrogen and inorganic salts under the usual conditions known for the cultivation of Streptomycetales in general and for the A 40926 producing strains in particular (c.f. also EP-A-177882 cited above) and adding an effective amount of the appropriate precursor to selectively enhance the production of antibiotic A 40926 factor A and/or factor $B_0$.

The appropriate precursor may be added to the fermentation in a continuous or discontinuous way during fermentation, or in pre-culture, or may be added to the cultivation medium before fermentation. It may be added directly, if suitably fluid at the fermentation temperature, or it may be added as a solution, suspension or emulsion, and preferably it is an aqueous solution of suspension.

An "effective amount" of appropriate precursor means an amount of precursor as defined above which, when added to the fermentation, gives a concentration of a selective precursor sufficient to produce the selective increase of the specific factor of antibiotic A 40926, without causing toxic effects to the growing culture of the producing microorganism.

The rate of addition of the precursor must be high enough to increase the yield of the desired factor to a considerable or optimum extent without however producing a toxic effect on the fermentation.

In general, it may be useful to feed an effective amount of the appropriate precursor in continuous or portionwise at the beginning, or during the production stage of the fermentation.

In some instances, it may be convenient to feed a mixture of some or all of the precursors of a certain factor in order to obtain a maximum result with minimum "toxic" effects on the culture.

Following fermentation, if desired, antibiotic A 40926 complex or the single factors A or $B_0$ PA or PB can be recovered according to the known procedures or obvious modifications thereof.

The nutrient fermentation media suitable for the fermentation of the A 40926 producing strain which can be used in the method of the invention, usually contain: a suitable carbon source which, for instance, may be selected from sugars (e.g. glucose, sucrose, maltose), polysaccharides (e.g. starch, dextrane) polyalcohols (e.g. glycerol, propylene glycol); suitable nitrogen sources which, for instance, may be selected from ammonium salts, asparagine, peanut meal, soybean meal, meat extract, tryptone, peptone, yeast hydrolyzate, yeast extract and corn step liquor; and inorganic salts. Among the inorganic salts which can be incorporated in the culture media there are the customary soluble salts capable of yielding sodium, potassium, iron, zinc, cobalt, magnesium, calcium, ammonium, chloride, carbonate, sulfate, phosphate, nitrate and the like ions.

Ordinarily, the antibiotic-producing strain is pre-cultured in a shake flask, then the culture is used to inoculate jar fermentors for production of substantial quantities of the antibiotic substances. The medium used for the pre-culture can be the same as that employed for larger fermentations, but other media can also be employed.

The fermentation is carried out for a time varying from 50 to 150 hours under submerged aerobic conditions at a temperature between 25° C. and 35° C., preferably between 27° C. and 33° C. The addition of the selectively effective amount of appropriate precursors can be made to the fermentative media before inoculation of the producing strain, or 24 to 48 hours after the fermentation is started. The addition may be made in one or several portions or in a continuous way.

According to a typical experiment embodying this invention, a culture of the A 40926 producing strain, maintained on oat-meal agar slants, is inoculated into a flask containing 100 ml of a vegetative medium. After about 72 hours, samples of the culture (5 milliliters) are used to inoculate a series of fermentation flasks containing 100 ml of fermentative medium, to which a selectively effective amount of precursor is added as appropriate. If concomitant increase of the two factors of A 40926 complex is desired, the appropriate precursors are added to the same fermentation flask. The fermentation is continued for additional 60 to 150 hours, and it is monitored at intervals by HPLC, then the fermentation cake is removed and samples of the broth are analyzed by HPLC.

The recovery of the antibiotic substances may be carried out as known in the art and described in detail in EP-A-177882. The recovery of the antibiotic substances of the invention from the fermentation broths of the producing microorganism is conducted according to known per se techniques which include extraction with solvents, precipitation by adding non-solvents or by changing the pH of the solution, partition chromatography, reverse-phase partition chromatography, ion-exchange chromatography, affinity chromatography and the like.

A preferred procedure includes an affinity chromatography on immobilized D-Alanyl-D-Alanine following by reverse-phase column chromatography. Immobilized D-Alanyl-D-Alanine matrices suitable for the present recovery process are disclosed in European Patent Application No. 83112555. The preferred matrix in the present process is D-Alanyl-D-alanine coupled with a controlled pore cross-linked polydextrane.

The fermentation broth can be subjected to the affinity chromatography directly after filtration or after a preliminary purification procedure. This latter procedure includes making the whole fermentation mass basic, preferably between pH 8.5 and 10.5, in order to solubilize the antibiotic substance adsorbed on the mycelium and then filtering. The clear filtrate is brought to pH 2.5–4.5 and filtered again in the presence of a filter aid. This filtrate is discarded while the recovered filtration cake is suspended in water, made basic, preferably at a pH between 8 and 9, and filtered. The filtration cake is re-subjected to the same procedure while the filtrates, which contain antibiotic A 40926, are pooled.

These filtrates or the filtered fermentation broths are then subjected to an affinity chromatography on immobilized D-Alanyl-D-Alanine, either in column or batchwise.

The binding of the antibiotic substance to the affinity matrix is preferably made at a pH of about 7.0–8.0 and its elution is performed at more basic pH values (preferably between 9.0 and 10.5) by means of an aqueous base. This aqueous base may be ammonia, a volatile amine, an alkali or alkali metal hydroxide or a basic buffered solution optionally in the presence of a polar organic solvent such as a polar water-miscible solvent as defined below.

After removing the impurities by rinsing the column with aqueous buffer pH 4–8, optionally containing salts, urea and/or water miscible solvents, the antibiotic a 40926 is eluted with the above eluting mixture. The crude antibiotic substance is then recovered preferably by removing water from the pooled antibiotic-containing fractions by azeotropical distillation with an organic solvent capable of forming minimum azeotropic mixtures with water, followed by addition of a non-solvent to precipitate the desired product.

Representative examples of organic solvents capable of forming minimum azeotropic mixtures with water are n-butanol, benzene, toluene, butyl ether, carbon tetrachloride, chloroform, cyclohexane, 2,5-dimethylfurane, hexane and m-xilene; the preferred solvent being n-butanol.

Examples of non-solvents are: petroleum ether, lower alkyl ethers, such as ethyl ether, propyl ether and butyl ether, and lower alkyl ketones such as acetone. Alternatively, the pooled antibiotic-containing fractions are concentrated to a small volume, preferably by azeotropical distillation with an organic solvent defined as above, and the resulting aqueous solution is lyophilized.

If the aqueous base employed in the elution is unvolatile, it may be necessary to neutralize and desalt the concentrate before precipitation or freeze-drying.

A convenient desalting procedure includes applying the antibiotic containing aqueous solution to a silanized silica gel column, washing with distilled water and eluting with a mixture of a polar water-miscible solvent and water.

Representative examples of polar water-miscible solvents are: water-soluble alcohols, (such a methanol, ethanol, iso-propanol, n-butanol), acetone, acetonitrile, lower alkyl alkanoates (such as ethyl acetate), tetrahydrofuran, dioxane and dimethylformamide and mixtures thereof; the preferred polar water-miscible solvent being acetonitrile.

Alternatively, desalting may be carried out by applying the antibiotic containing solution to the above described affinity column, washing with distilled water and eluting with a volatile aqueous base as described above for the elution of the affinity chromatography. The product so obtained is antibiotic A 40926 complex. If necessary, it may be further purified or subjected as such to the separation of its factors A, B, $B_o$, PA and PB.

A convenient procedure to obtain a pure antibiotic A 40926 complex is represented by a further purification of the complex as obtained above on an affinity chromatography column. The same stationary phase as above (immobilized D-Alanyl-D-Alanine) is generally used and the desired antibiotic substance is eluted by following the affinity chromatography procedure on immobilized D-Alanyl-D-Alanine described above. A preferred immobilized D-Alanyl-D-Alanine is Sepharose-E-Aminocaproyl-D-Alanyl-D-Alanine, a preferred equilibrating mixture is 0.16% (w/v) ammonia containing 2M NaCl adjusted to pH 7–8, a preferred rinsing solution is 0.16% (w/v) ammonia containing 2M NaCl adjusted to pH 8–9.5, a preferred eluting mixture is 0.16% (w/v) ammonia containing 2M NaCl adjusted to pH 10.5–12 and a most preferred eluting mixture is the above mixture adjusted to pH 11.5.

The antibiotic A40926 factors, namely antibiotic A 40926 factor A, antibiotic 40926 factor B, antibiotic A 40926 factor Bo, antibiotic A 40926 factor PA and antibiotic A 40926 factor PB are isolated from an aqueous solution of antibiotic A 40926 complex by column chromatography and preferably by reverse-phase column chromatography. The preferred stationary phase in the case of reverse-phase column chromatography is silanized silica gel. Good results may be obtained however also with column chromatography on non-functionalized polystyrene and acrylic resins such as those sold under the trade names Amberlite XAD-2, XAD-4, XAD-7 and XAD-8 (Rohm and Haas) or Diaion HP 20 (Mitsubishi). In case the reverse-phase purification step is accomplished by means of a silanized silica gel as the stationary phase, the column is preferably pre-equilibrated with a buffered aqueous solution at pH between 4 and 9 and preferably between 5.5–6.5 and then eluted with a linear gradient of a polar water-miscible solvent in the same buffered solution. Representative examples of polar water-miscible solvents are: water-soluble alcohols, (such as methanol, ethanol, iso-propanol, n-butanol), acetone, acetonitrile, tetrahydrofuran, dioxane and dimethylformamide and mixtures thereof; the preferred polar water-miscible solvent being acetonitrile.

The eluted fractions are assayed for their antibiotic content by means of the usual bioassays such as paper-disc or agar-diffusion assays, on susceptible microorganisms. Examples of susceptible organisms are *Bacillus subtilis* and *S. aureus*.

The chromatography is also conveniently monitored by TLC or HPLC techniques.

A preferred HPLC technique is represented by a reverse-phase HPLC using a column of porous and spheric particles of silanized silica gel functionalized with C-18 alkyl groups having a diameter preferably of 5 micrometers (such as 5 μm Ultrasphere® ODS Altex; Beckman Co.) a pre-column which is a silica gel functionalized with C-18 alkyl groups (such as RP 18 Brownlee Labs) and an eluent which is a linear gradient mixture of a polar water miscible solvent, such as one of those described above, in a aqueous buffered solution.

Preferably this solution is adjusted to a pH 5–7. A most preferred eluent is represented by a linear gradient from 5 to 60% of eluent B in eluent A wherein eluent A is a mixture of acetonitrile/aqueous buffer, pH 5–7, 10:90 and eluent B is a mixture of acetonitrile/aqueous buffer, pH 5–7, 70:30. As known in the art, many substances can be used as internal standards. A very convenient one is, in this case, Teicoplanin $A_2$ component 2 (Gruppo Lepetit S. p. A.) which has a retention time close to the compounds of the invention in this HPLC system. This standard substance is known and has been described in GB-A-2121401.

Fractions with a similar antibiotic content are pooled and desalted as described above to give essentially pure antibiotic A 40926 factor A, factor B, factor $B_o$, factor PA, and factor PB.

Essentially pure antibiotic A 40926 factor A and antibiotic A 40926 factor B, antibiotic A 40926 factor Bo, antibiotic A 40926 factor PA and antibiotic A 40926 factor PB are obtained from those fractions containing them by a variety of known techniques such as lyophilization, precipitation by non-solvents or precipitation by changing the pH of the aqueous solution.

A convenient procedure includes adding a solvent capable of forming azeotropic mixtures with water, removing water by azeotropic distillation and then collecting by filtration the precipitate obtained after addition of a non-solvent like those described above.

For veterinary application, the whole fermentation cake or concentrated broth can be used.

The addition of the precursor to the fermentation is such that it does not affect considerably its predetermined pH range. Thus, for instance, when free acid precursors are added directly to the medium, the pH is maintained under control by buffering the medium or by immediate neutralization with bases which are non-toxic to the microorganism.

When the precursor to be added is an aminoacid, it may be supplied to the fermentation as an aqueous solution of its salts with acids or bases which are non-toxic to the producing microorganism, e.g. hydrochlorides and sodium salts, even if in many instances the aminoacid may conveniently be added as a solution of the "internal salt". Both racemic mixtures and optically active isomers can be used as precursors.

However, in general, the addition of the L-form gives higher yields than the corresponding D-form.

A preferred embodiment of the process of this invention is therefore represented by the use of the L-form of the aminoacid precursor for enhancing the concentration of factor $B_0$ or PB (L-valine, a salt or an ester thereof), and/or factor A or PA (L-isoleucine, a salt or an ester thereof) of antibiotic A 40926 complex. According to this preferred embodiment, it is also possible to increase the percentage of factor A or $B_0$ in the fermentation product over 80% of the complex.

With lower alkanoic acid precursors (2-methylbutyric acid, isobutyric acid, alpha-keto-isovaleric acid, and alpha-keto-beta-methylvaleric acid) the addition may be made through an aqueous solution of their salts with non-toxic bases; ammonium and sodium salts are usually preferred.

When esters of the above lower alkanoic acids and unsaturated fatty acids with mono-hydroxy lower alkanols are employed as precursors, said esters are usually derived from methanol, ethanol and propanol, although esters with $C_4$–$C_6$ alkanols may also be employed. In this case, the $C_4$–$C_6$ alkanol must be different from that which may act as precursor for the other factor, (isobutanol, 2-methylbutanol or propanol), unless concomitant increase of the other factor is desired.

Alkanol precursors such as isobutanol, 2-methylbutanol and n-propanol are usually added as such to the fermentation. However, they can be supplied also as esters of acids which are non-toxic to the microorganism. These acids must be different from those which may act as precursors for the other A 40926 factor unless concomitant increase of the other factor is desired. Usually, esters with linear ($C_2$–$C_4$) alkanoic acids such as acetic, propionic and butyric acid are preferred.

The "selectively effective amount" to be added to the fermentation medium according to this invention depends on the type of precursor. Usually, with the esters of the lower alkanoic acids (isobutyric acid, 2-methylbutyric acid) amounts that yield a concentration of the acid into the fermentation medium ranging between 0.1 g/l and 5 g/l are employed, with the range between 0.1 g/l and 1 g/l being preferred. With lower alkanols (isobutanol, 2-methylbutanol, n-propanol) or their esters with acids which are non-toxic to the microorganism, amounts that yield a concentration of the alcohol ranging between 0.5 g/l and 5 g/l are usually employed, with the range between 1 g/l and 2 g/l being preferred.

With the aminoacids (valine, isoleucine) and the keto-acids (alpha-keto-isovaleric acid, alpha-keto-beta-methylvaleric acid) or their salts with acids and bases the "selectively effective amount" added to the fermentation medium usually ranges between 0.2 g/l and 5 g/l, and preferably between 0.5 g/l and 4 g/l; the most preferred range being between 2 and 4 g/l.

In the case where the lower alkanoic acids (e.g. isobutyric acid, 2-methylbutyric acid), or their salts are directly added to the fermentation medium, the "selectively effective amount" usually ranges between 0.1 g/l and 2.5 g/l, with the range between 0.3 g/l and 1.5 g/l being preferred.

Concentrations higher than those indicated above may still be effective in enhancing the relative percentage of one of the A 40926 factors but, in general, the overall yield is depressed because of toxic effects on the culture.

EXAMPLE 1

A culture of Actinomadura sp. ATCC 39727 on agar slant is used to inoculate a 500 ml Erlenmeyer flask containing 100 ml of the following medium:

| | |
|---|---|
| Meat extract | 5 g |
| Autolysed yeast | 5 g |
| Peptone | 5 g |
| Casein hydrolysed | 3 g |
| Glucose | 20 g |
| NaCl | 1.5 g |
| $CaCO_3$ | 4 g |
| Distilled water q.s. | 1000 ml |

The flask is incubated at 28° C. on a rotary shaker at 200 rpm for about 72 hours and then the mycelium is collected by centrifugation, washed twice with sterile deionized water and suspended in 100 ml of sterile deionized water. 2 Ml of this suspension are used to inoculate a 500 ml Erlenmeyer flask containing 100 ml of the above medium and the appropriate precursor is added. The antibiotic production is monitored by the paper-disc agar diffusion method using *B. subtilis* on a minimal medium as the test organism.

After 72 hours of cultivation on a rotary shaker at 200 rpm, the fermentation cake is removed by filtration and the filtrate is passed through a Sepharose-Epsilon-aminocaproyl-D-Alanyl-D-Alanine column (0.5 ml of resin/0.3 ml of broth) and eluted with 1% (w/v) ammonia hydrate. The fractions which contain antibiotic A 40926 are pooled and left one day at room temperature, then are analyzed by HPLC according to the following procedure:

| | |
|---|---|
| column: | Silanized silica gel Ultrasphere ODS (5 micrometer) Altex (Beckman) 4.6 mm (i.d.) × 250 mm |
| pre-column: | Silanized silica gel Brownlee Labs RP 18 (5 micrometer) |
| eluent A: | $CH_3CN$ 10% } adjusted at (2.5 g/l) $NaH_2PO_4.H_2O$ 90% } pH 6.0 |
| eluent B: | $CH_3CN$ 70% } adjusted at (2.5 g/l) $NaH_2PO_4.H_2O$ 30% } pH 6.0 |
| elution: | linear gradient from 5% to 60% of eluent B in eluent A1, in 40 min |
| flow rate: | 1.8 ml/min |
| U.V. detector: | 254 nm |
| internal standard: | Teicoplanin $A_2$ component 2, $R_t$ = 20.3 min (Gruppo,Lepetit S.p.A.) |
| relative retention times: | A 40926 factor A 1.12 A 40926 factor $B_0$ 1.22 A 40926 factor $B_1$ 1.27 A 40926 factor PA 1.15 A 40926 factor PB 1.27 |

Percentage distribution

The components are separated by the above procedure and their relative distribution is obtained as a percent of the total of the two peaks by the area percentage method. The results of representative experiments are reported below:

| Precursor added (NM) | Total conc. (microgram/ml) | % $\dfrac{\text{Factor A}}{\text{Factor A + Factor } B_0}$ | % $\dfrac{\text{Factor } B_0}{\text{Factor A + Factor } B_0}$ |
|---|---|---|---|
| None (—) | 24–60 | 22–36 | 78–64 |
| L-valine | | | |

-continued

| Precursor added (NM) | Total conc. (microgram/ml) | % $\frac{\text{Factor A}}{\text{Factor A + Factor B}_0}$ | % $\frac{\text{Factor B}_0}{\text{Factor A + Factor B}_0}$ |
|---|---|---|---|
| 8 L-isoleucine | 24 | 5 | 95 |
| 8 Isobutanol | 13 | 59 | 41 |
| 5 n-Propanol | 30–57 | 3–18 | 97–81 |
| 5 2-Methyl-1-butanol | 34 | 51 | 48 |
| 5 | 34 | 47 | 53 |

By essentially following the above procedure but rapidly neutralizing the ammonic eluates instead of leaving them aside for 24 h, the antibiotic A 40926 factor PA and/or PB are obtained, instead of factor A and $B_0$, respectively.

The percentages and the results are substantially as reported above for factors A and $B_0$.

We claim:

1. A process for preparing antibiotic A40926 complex containing factor A, wherein the strain Actinomadura Sp. ATCC 39727 or a mutant of Actinomadura Sp. ATCC 39727 is cultured under submerged aerobic conditions in an aqueous nutrient culture medium containing assimilable sources of carbon, nitrogen, and inorganic salts, to provide the A40926 complex, the improvement comprising: an enrichment in the amount of factor A in the A40926 complex wherein the enrichment is achieved by cultivating the strain in a medium comprised of glucose, meat extract, yeast, peptone, casein, inorganic salts, and an added amount of a precursor, at a temperature between about 27° C. and 33° C., wherein the amount of precursor in the medium is from about 4 to about 20 mM and the precursor is selected from the group consisting of:
   a) isoleucine, the salt of isoleucine with an acid or a base which is non-toxic to the culture;
   b) n-propanol, an ester of n-propanol formed with a linear $C_1$–$C_6$ alkanoic acid, which ester is non-toxic to the culture; and
   c) 2-methyl-1-butanol, an ester of 2-methyl-1-butanol formed with a linear $C_1$–$C_6$ alkanoic acid, which ester is non-toxic to the culture;
until the amount of factor A in the medium is equal to about 47% to about 59% of the total factors A and $B_o$ of the complex as monitored chromatographically, then recovering the complex from the culture medium by separating the complex enriched in factor A from the medium and, isolating the complex via chromatography.

2. The process according to claim 1 wherein the precursor is isoleucine or the salt of isoleucine.

3. The process according to claim 1 wherein the precursor is n-propanol or the ester of n-propanol.

4. The process according to claim 1 wherein the precursor is 2-methyl-1-butanol or the ester of 2-methyl-1-butanol.

5. The process according to claim 1 wherein the antibiotic A40926 complex enriched in factor A is isolated from the culture medium by affinity chromatography.

6. A process for preparing antibiotic A40926 complex containing factor $B_o$, wherein the strain Actinomadura Sp. ATCC 3 9727 or a mutant of Actinomadura Sp. ATCC 39727 is cultured under submerged aerobic conditions in an aqueous nutrient culture medium containing assimilable sources of carbon, nitrogen, and inorganic salts, to provide A40926 complex, the improvement comprising: an enrichment of factor $B_o$ in the A40926 complex wherein the enrichment is achieved by cultivating the strain in a medium comprised of glucose, meat extract, yeast, peptone, casein, inorganic salts, and an added amount of a precursor, at a temperature between about 27° C. and 33° C., wherein the amount of added precursor in the medium is from about 4 to about 10 mM and the precursor is selected from the group consisting of:
   a) valine, the salt of valine formed with an acid or a base which is non-toxic to the culture; and
   b) isobutanol, an ester of isobutanol formed with a linear $C_1$–$C_6$ alkanoic acid, which ester is non-toxic to the culture;
until the amount of factor $B_o$ is equal to about 81% to about 97% of the total of factors A and $B_o$ of the complex as monitored chromatographically, then recovering the complex from the culture medium by separating the complex from the medium, and isolating the complex via chromatography.

7. The process according to claim 6 wherein the precursor is valine or the salt of valine.

8. The process according to claim 6 wherein the precursor is isobutanol or the ester of isobutanol.

9. The process according to claim 6 wherein the antibiotic A40926 complex enriched in factor $B_o$ is isolated from the culture medium by affinity chromatography.

* * * * *

UNITED STATES PATENT AND TRADEMARK OFFICE
CERTIFICATE OF CORRECTION

PATENT NO : 5,843,679

DATED : December 1, 1998

INVENTOR(S) : Selva et al.

It is certified that error appears in the above-identified patent and that said Letters Patent is hereby corrected as shown below:

On the title page, item
[75] "Giovanni Cassani" should be --Ciovanni Cassani--.

[30] "Sep. 11, 1988" should be --Sep. 11, 1986--.

Signed and Sealed this

Sixteenth Day of November, 1999

*Attest:*

Q. TODD DICKINSON

*Attesting Officer*   *Acting Commissioner of Patents and Trademarks*